United States Patent
Wallenstein et al.

(10) Patent No.: US 10,077,404 B2
(45) Date of Patent: Sep. 18, 2018

(54) PROCESS FOR EVALUATING THE CATALYTIC PERFORMANCE OF A POROUS SOLID

(71) Applicant: W. R. Grace & Co.-Conn., Columbia, MD (US)

(72) Inventors: Dieter Wallenstein, Gau-Algesheim (DE); Stefan Brandt, Nubloch (DE)

(73) Assignee: Grace GmbH, Worms (DE)

( * ) Notice: Subject to any disclaimer, the term of this patent is extended or adjusted under 35 U.S.C. 154(b) by 0 days.

(21) Appl. No.: 15/532,426

(22) PCT Filed: Dec. 1, 2015

(86) PCT No.: PCT/EP2015/078224
§ 371 (c)(1),
(2) Date: Jun. 1, 2017

(87) PCT Pub. No.: WO2016/087446
PCT Pub. Date: Jun. 9, 2016

(65) Prior Publication Data
US 2017/0267934 A1 Sep. 21, 2017

Related U.S. Application Data

(60) Provisional application No. 62/087,961, filed on Dec. 5, 2014.

(51) Int. Cl.
*C10G 11/18* (2006.01)
*G01N 13/00* (2006.01)
(Continued)

(52) U.S. Cl.
CPC ........... *C10G 11/187* (2013.01); *G01N 13/00* (2013.01); *G01N 15/082* (2013.01); *G01N 30/89* (2013.01);
(Continued)

(58) Field of Classification Search
CPC .... C10G 11/187; G01N 15/082; G01N 13/00; G01N 30/89
See application file for complete search history.

(56) References Cited

U.S. PATENT DOCUMENTS

2002/0187555 A1* 12/2002 Jonker et al. .......... G01N 21/00
436/37
2007/0196924 A1 8/2007 Wang .............................. 436/34

FOREIGN PATENT DOCUMENTS

EP 1393045 4/2011 ............. G01N 15/08

OTHER PUBLICATIONS van Deemter, J. J.; Zuiderweg, F.J.; Klinkenberg, A. "Longitudinal Diffusion and Resistance to Mass Transfer as Causes of Nonideality in Chromatography" Chemical Engineering Science, v 5, p. 271-289 (1956).

(Continued)

*Primary Examiner* — Brian A McCaig
(74) *Attorney, Agent, or Firm* — Charles A. Cross; Beverly J. Artale (57) ABSTRACT

Process for evaluating the catalytic performance of a porous solid using a vapor diffusion technique, where a probe molecule and a molecule for dead-time determination is injected into a carrier gas that is then contacted with the porous solid in a vessel, where a detector analyzes the peak width and retention time of a probe molecule and the retention time of the molecule for dead-time determination in the gas exiting the vessel.

23 Claims, 6 Drawing Sheets

(51) Int. Cl.
  *G01N 15/08* (2006.01)
  *G01N 30/89* (2006.01)
(52) U.S. Cl.
  CPC . *C10G 2300/708* (2013.01); *G01N 2013/003* (2013.01)

(56) References Cited

OTHER PUBLICATIONS

Kortunov, P.; Vasenkov, S.; Karger, J.; Fe Elia, M.; Perez, M.; Stocker, M.; Papadopoulos, G.K.; Theodorou, D.; Drescher, B.; McElhiney, G.; Befnauer, B.; Krystl, V.; Kocirik, M.; Zikanova, A.; Jirglova, H.; Berger, C.; Glaser, R.; Weitkamp, J.; Hansen, E.W. "Pulsed-Field Gradient Nuclear Magnetic Resonance Study of Transport Properties of Fluid Catalytic Cracking Catalysts" Magnetic Resonance Imaging, v 23, p. 233-237 (2005).

Ogura, Maseru; Shinomiya, Shin-ya; Tateno, Junko; Nara, Yasuto; Nomura, Mikihiro; Kikuchi, Eiichi; Matsukata, Masahiko "Alkali-Treatement Technique—New Method for Modification of Structural and Acid-Catalytic Properties of ZSM-5 Zeolites" Applied Catalysis A: General, v 219, p. 33-43 (2001).

Schuurman, Y.; Delattre, C.; Pitault, I.; Reymond, J.P.; Forissier, M. "Effect of Coke Deposition on Transport and Sorption in FCC Catalysts Studied by Temporal Analysis of Products" Chemical Engineering Science, v 60, p. 1007-1017 (2005).

Tailleur, Robert Galiasso; Platin, Jose Bonilla "Conversion of Propylene into Cyclohexane on PtGaZr/SiO2 Catalyst" Catalysis Today, v 130, p. 527-536 (2008).

PCT Search Report and Written Opinion for PCT/EP2015/078224; dated Jun. 9, 2016.

U.S. Appl. No. 62/087,961, filed Dec. 5, 2014.

* cited by examiner

PROCESS FOR EVALUATING THE CATALYTIC PERFORMANCE OF A POROUS SOLID

FIELD OF THE INVENTION

The invention relates to a process for evaluating the catalytic performance of a porous solid. More particularly, the invention relates to a process for evaluating the catalytic performance of a fluidized catalytic cracking catalyst using a vapor diffusion technique.

BACKGROUND OF THE INVENTION

Fluidized catalytic cracking ("FCC") is a key process in modern petrochemical refineries due to the large volume of gasoline and distillate fuels that it generates. An integral part of FCC operation is the catalyst, which is particularly designed in view of a unit's product needs, feedstock and operating limitations. The health of the FCC catalyst is typically monitored by taking samples of the circulating catalyst (the so-called equilibrium catalysts) and performing tests to measure physical/chemical properties and the activity of the catalyst under standard laboratory testing. Normally, data from these measurements provides relevant information as to yield changes resulting from changes in the catalyst itself. These changes can include damage to the catalyst suffered as a result of high temperatures or the effects of metals contamination. Metals contamination has long been known to poison the catalytically active sites of the FCC catalyst as well as sometimes serving as catalysts of undesirable reactions themselves. For example, nickel deposited on the surface of an FCC catalyst itself acts as a catalyst to dehydrogenate FCC feedstocks, resulting in higher hydrogen and coke production. This damage or contamination of the FCC catalyst can be tracked by testing the circulating inventory of catalyst, as mentioned above. However, periodically poor catalyst performance will be observed with little corresponding explanation in the catalyst properties. This situation can occur from pore blockage of the FCC catalyst caused by particular forms of iron, sodium, calcium or coke and coke precursors (Conradson Carbon Residue) that are present in the feedstock, which deposit on the surface of the catalyst in such a way as to block the catalyst pores without showing significant changes in the bulk metal content in the equilibrium catalyst properties. Correlating the accessibility of porous materials has been disclosed in EP1393045, however, this technique uses probe molecules dissolved in a solvent, where the uptake of the probe molecule from the solvent solution is measured. Thus, it measures a relative "accessibility," not an actual effective diffusivity of the probe molecule. In addition, gas-phase measurement of diffusion in porous solids is possible by conventional techniques using noble gases as probe molecules. However, these methods do not adequately discriminate among samples for the purpose of diagnosing pore blockage in FCC catalysts because the molecules are much smaller than those encountered commercially, and they do not operate at conditions that adequately simulate those found in operating FCC's.

Thus, there is a need for a process that evaluates the catalytic performance of an FCC catalyst using a vapor diffusion technique. The present disclosure now provides such a method.

SUMMARY OF THE INVENTION

The subject matter of the present disclosure relates to a process for evaluating the catalytic performance of an FCC catalyst using a vapor diffusion technique.

In one embodiment, the present disclosure provides a process for evaluating the catalytic performance of a porous solid. The process comprises first injecting a vaporized probe molecule and a molecule for dead-time determination into a carrier gas having a first flowrate, to form a combined gas. The combined gas is then fed to a vessel containing the porous solid, where the combined gas contacts the porous solid, to form a contacted gas. Next, the contacted gas is analyzed after it exits the vessel in a detector to measure the peak-width and the retention time of the probe molecule, and the retention time of the molecule for dead-time determination. The probe molecule/molecule for dead-time injection step, porous solid contacting step and the contacted gas analysis step are repeated, where for each set of repeated steps the carrier gas has a flowrate different than the first flowrate and other succeeding flowrates. Finally, an effective diffusion coefficient is calculated for the porous solid, which is reactively inert toward the probe molecule.

In another embodiment, the present disclosure provides a process for adjusting fresh catalyst additions to an FCC unit. The process comprises first injecting a vaporized probe molecule and a molecule for dead-time determination into a carrier gas having a first flowrate, to form a combined gas. The combined gas is then fed to a vessel containing deactivated FCC catalyst, wherein the combined gas contacts the deactivated FCC catalyst, thereby forming a contacted gas, the probe molecule being reactively inert to the deactivated FCC catalyst. Next, the contacted gas is analyzed after it exits the vessel in a detector to measure the peak-width and the retention time of the probe molecule, and the retention time of the molecule for dead-time determination. The probe molecule/molecule for dead-time injection step, porous solid contacting step and the contacted gas analysis step are repeated, where for each set of repeated steps the carrier gas has a flowrate different than the first flowrate and other succeeding flowrates. An effective diffusion coefficient is then calculated for the FCC catalyst. Finally, the fresh catalyst additions to the FCC unit are changed based on the difference between a target effective diffusion coefficient and the calculated effective diffusion coefficient.

BRIEF DESCRIPTION OF THE DRAWINGS

The subject matter of the present disclosure will be more fully understood from the following detailed description, taken in connection with the accompanying drawings, in which.

DETAILED DESCRIPTION OF THE INVENTION

The inventive method evaluates the catalytic performance of an FCC catalyst using a vapor diffusion technique.

FCC Catalytic System

The FCC produces gasoline and distillate fuels as desired products by contacting hot, regenerated catalyst from the FCC regenerator with hydrocarbon feed in the FCC riser. The hydrocarbon feed vaporizes, depositing most metals present in the feed on the surface of the catalyst. The vaporized hydrocarbon feed reacts on the surface and in the pores of the catalyst to form smaller (cracked) molecules. During the reactions in the FCC riser, coke is formed and deposited on the active surface of the catalyst. The "coked" catalyst is separated from the product vapors, stripped with steam and then flows back to the regenerator. In the regenerator, the coke (carbon) deposited on the catalyst surface is burned to levels below 0.5 wt %, preferably to levels below 0.1 wt %.

The activity of the FCC catalyst circulating in the unit inventory depends upon its initial activity, hydrothermal deactivation that occurs in the unit, poisoning by metals or other feed contaminants that deactivate the catalyst, and the fresh catalyst addition rate. To increase the activity of the circulating FCC catalyst inventory, the fresh catalyst addition rate can be raised. If this rate exceeds the normal catalyst losses of the unit, for example through losses from the unit cyclones, equilibrium catalyst can be withdrawn to maintain a constant unit inventory. The increase in fresh catalyst addition rate raises the activity of the unit inventory since it increases the inventory fraction of younger, more-active catalyst. It also reduces the overall metals level of the circulating inventory. When metals contamination has blocked the pores of the FCC catalyst, e.g., by iron, the bottoms upgrading ability of the catalyst is negatively impacted. In this case, increased catalyst additions will reduce the percent of catalyst inventory having blocked pores, and thus improve bottoms upgrading. In this way, measurement of the effective diffusion coefficient for the equilibrium catalyst can be used as an objective measure upon which to modulate fresh catalyst additions, similar to the manner in which MAT activity is typically used.

Porous Solid-FCC Catalyst

The porous solids used in the process of the present disclosure are fine powders of oxides of silicon and aluminium having a pore volume of 0.2 to 0.7 cm$^3$/g, surface area of 10 to 500 m$^2$/g, and an average particle size of 20 to 100 μm. The porous solid is reactively inert with respect to the probe molecule. For the purpose of this specification, the term "reactively inert" with respect to: (i) the probe molecule/carrier gas, (ii) the molecule for dead-time determination/carrier gas, and the porous solid, means that at the temperature of the diffusion measurement, the porous solid does not crack, dehydrogenate, condense, isomerize, or decompose (i) the probe molecule or (ii) the molecule for dead-time determination; and (i) the probe molecule, or (ii) the molecule for dead-time determination do not permanently adsorb or absorb onto the porous solid. Preferably, the porous solid is selected from FCC catalysts. More preferably, the porous solid is an FCC catalyst containing a zeolite, an active matrix, clay and a binder, the catalyst having an alumina content of 20 to 70% and a silicate content of 25 to 75%. FCC catalyst particles have on average a diameter of 50-110 μm, and contain approximately 20-60% zeolite crystals of about 1 μm diameter dispersed in the matrix. The zeolite is the primary catalytic component for selective cracking reactions and is a synthetic faujasite crystalline material. It includes material that is manufactured in the sodium form (Standard-Y) by crystallization of sodium aluminate and sodium silicate, followed by washing; and ultrastable Y ("USY"), produced by increasing the silicon/aluminium atomic ratio of the parent standard-Y zeolite via a dealumination process. The resulting USY zeolite is much more stable to the hydrothermal deactivation in commercial FCC units than Standard Y zeolite. The zeolite crystal "cage" for USY zeolite has a fresh unit cell size of approximately 24.40-24.65 Å and a SiO$_2$/Al$_2$O$_3$ mole ratio of about 5.5. The zeolites can be treated with cations, typically rare earth mixtures, to remove sodium from the zeolite framework, which increases activity and further stabilizes the zeolite to deactivation in the FCC unit. The zeolite possesses pores in the 7.4-12 Å range, allowing only penetration of molecules smaller than 10.2 Å. After hydrothermal deactivation in the commercial FCC, the zeolite acquires pores in the 20 to 800 Å range. Such pores reside primarily in the so-called mesopore range (20 to 500 Å) range. Surface area corresponding to the zeolite, i.e., surface area corresponding to pores in the range of <20 Å, typically ranges from 20 to 300 m$^2$/g, preferably from 60 to 200 m$^2$/g.

The catalyst can also include active matrix. This is catalytically active, porous silica-alumina material, however, in contrast to the zeolite, it is non-crystalline, i.e., amorphous. The active matrix contains pores in the mesopore range (20-500 Å) as well as macropores (>500 Å). Surface area corresponding to the matrix, i.e., the surface of pores in the range of from 20 to 10000 Å typically ranges from 10 to 150 m$^2$/g, preferably from 90 to 150 m$^2$/g. Because of the molecular size restrictions for entering the zeolite pores, and thus for zeolite cracking, the presence of active matrix serves the important purpose of cracking molecules that are too large for diffusion into the zeolite pores. In the active matrix, these large molecules can be cracked into reaction products that are small enough to then navigate the zeolite pores for further coke selective cracking. Without the matrix, the large molecules would thermally condense to coke on the surface of the catalyst. In this way, it can be understood that the performance of an FCC catalyst is fundamentally dependent on its design in terms of a balance of zeolite and matrix components, particularly for use with heavier feedstocks. If matrix is not present in sufficient quantities, large molecules cannot diffuse into the zeolite pores to be cracked, and so form coke. If zeolite is not present in sufficient quantities, coke selective cracking cannot occur, so again coke is formed. The synergism between the zeolite and matrix lies in the relationship between their pore structures.

The catalyst also includes clay. While not generally contributing to the catalytic activity, clay provides mechanical strength and density to the overall catalyst particle to enhance its fluidization.

Finally, the catalyst contains a binder. This is the glue that holds the zeolite, matrix and clay together. The binders are typically silica-based, alumina-based or clay-based. The silica-based binders have very little or no activity. The alumina-based and clay-based binders have some bottoms cracking ability.

The complete FCC catalyst has a total pore volume of 0.2 to 0.6 cm$^3$/g, where the water pore volume is determined by adding water to a dry sample of a given weight. The water in between the particles was removed by centrifugation. The water pore volume represents the volume of water that displaces the air in the pores.

Figure 1:
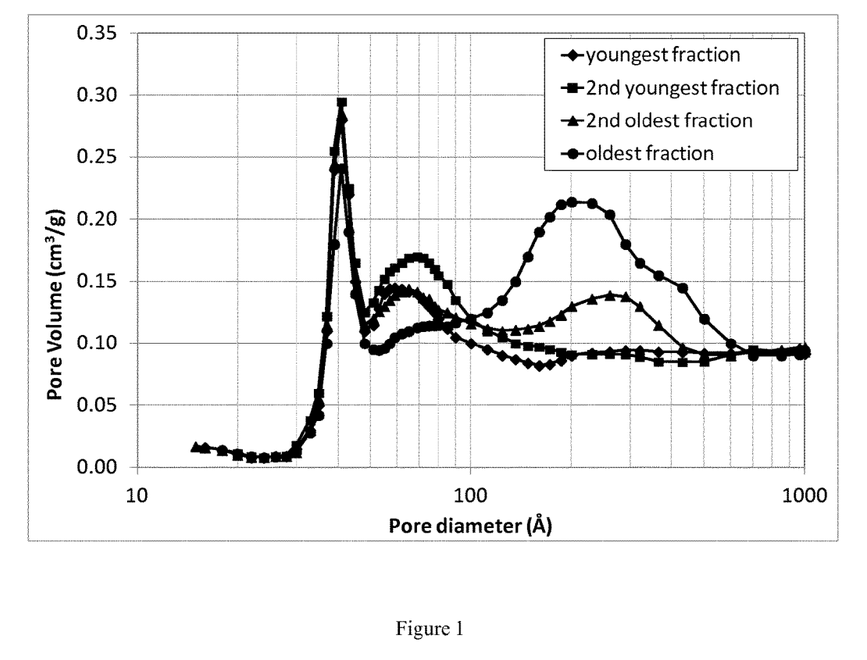
FIG. 1 illustrates BJH pore volume distributions (nitrogen sorption) of age fractions obtained from density separations of an equilibrium catalyst.

During FCC operation, continuums of pore openings and pores of different sizes evolve in the catalyst, whereby the pores ascribed to the mesopores of the zeolite (20-500 Å) are enlarged with particle age, while matrix pores decrease. Such a continuum of pore volume distribution, determined with nitrogen sorption on an equilibrium catalyst and separated by density separation in age fractions is illustrated in FIG. 1. The pore structure displayed originates from the zeolite and the matrix. The zeolite mesopores that evolve during the degradation process are represented by the peaks between 100-1000 Å. The matrix contributes to the whole >40 Å region and in FIG. 1, the given example its contribution is pronounced in the 50-100 Å range.

Diffusion in FCC Catalysts

The diffusion in FCC catalysts is classified in terms of three distinct resistances to mass transfer, depending on the pore size:

the micropore resistance of the zeolite, meso- and macropore diffusional resistance ascribed to the matrix, and the resistance related to the outer layer of the catalyst (surface barrier resistance).

The pore volume distribution illustrated in FIG. 1 shows the pore structure of FCC equilibrium catalysts to be in the mesopore and macropore range. Therefore, the pore sizes of zeolite and matrix overlap, thereby complicating the discrimination of their individual contributions to zeolite and matrix diffusion in FCC catalysts.

In the FCC process, diffusion is supported by flow and concentration gradients. This kind of diffusion is the so-called transport diffusion. Diffusion measurements by inverse gas chromatography (iGC) measure such a diffusion type. iGC refers to the stationary phase and its interaction with a pulse of probe molecules moving through it in a carrier gas flow. iGC is generally considered an appropriate tool for measuring transport diffusion, since the experiments are performed in a flowing system and under concentration gradients.

According to these considerations, iGC appears to be an appropriate method for diffusion investigations on FCC catalysts because it is a transport diffusion type measurement simulating to a certain degree diffusion in an actual FCC reaction zone.

In the current process, the measured diffusion in FCC catalysts is referred to as effective diffusion coefficient. The effective diffusion coefficient describes diffusion through the pore space of porous media. It is macroscopic in nature, because it is not individual pores, but only the transport-available porosity. This equals the total porosity less the pores which, due to their size, are not accessible to the diffusing particles, and less dead-end and blind pores (i.e. pores without being connected to the rest of the pore system).

FCC Feedstocks

Various feedstocks can be cracked in the FCC. Most prevalent are the gas oils, either virgin or cracked. Heavier feedstocks such as vacuum resid, atmospheric resid and deasphalted oil can also be processed. While contaminant metals can be present in all the above feedstocks, they are most prevalent in the heavy streams. The FCC feedstocks are introduced as liquids, however, they vaporize when they contact hot catalyst flowing from the regenerator, the FCC cracking reactions then proceeding in the vapor phase. However, the metals are deposited quantitatively on the surface of the catalyst. Because the catalyst inventory in an FCC can be quite large (100+ tons), the residence time in the FCC unit can be weeks or months. This means that metals will continue to accumulate on the catalyst the entire time it flows through the unit.

Metals such as nickel catalyse dehydrogenation reactions, which result in gas and coke being produced. Vanadium catalyses dehydrogenation reactions to a certain extent, however, it also attacks the zeolite structure itself. Sodium and calcium also attack the zeolite, but in addition, interact with the silica/alumina structure to reduce active surface area. Iron present in the feed can also result in dehydrogenation reactions, but more importantly it has been found to obstruct the pores of the catalyst. When this happens, large molecules cannot diffuse into the pores of the catalyst, and so cannot be cracked. Iron compounds present in the FCC feed are typically present as porphyrins, naphthenates or inorganic compounds in amounts of 0 to 10000 mg/kg. However, different iron-containing compounds obstruct the pores to different degrees, so that merely monitoring the total amount of iron present on the equilibrium catalyst does not provide an adequate indication of the level of obstruction present. In these instances, an evaluation of the diffusion in the equilibrium catalysts must be utilized.

Probe Molecule

The probe molecule used in the inventive process is particularly chosen to optimally reflect the diffusion of vaporized FCC feedstock molecules in the pores of the FCC catalyst, without reacting with the catalyst. This requires a probe molecule preferably having a size of 5-15 Å, more preferably having a size of 8-10 Å. If the size of the probe molecule is too small, it will not adequately discriminate flow in partially-blocked pores. If the size of the probe molecule is too large, it will have difficulty diffusing into the catalyst pores at all. Similarly, the probe molecule should have a boiling point of 150° C. to 300° C. This ensures that the probe molecule can be maintained as a vapor during the testing. Preferably, the probe molecule is selected from 1,2,4-trimethylcyclohexane, t-decaline, adamantan or phenanthrene. More preferably, the probe molecule is 1,2,4-Trimethylcyclohexane.

The probe molecule can either be vaporized directly into the carrier gas or first dissolved in a solvent such as $CS_2$ or acetone, and then vaporized into the carrier gas.

Molecule for Dead Time Determination

For applying the van Deemter model in the calculation of effective diffusion coefficient, the net hold-up time of a molecule in the FCC catalyst due to diffusion limitations and the linear velocity of the carrier gas in the FCC catalyst bed and GC column are needed. For this determination a molecule without any diffusion limitations in the pores of the FCC catalyst and non-reactive with the FCC catalyst active sites is needed. Preferably, this molecule is selected from methane, ethane or propane. More preferably, the molecule is methane.

Injection of Carrier Gas

The carrier gas used in the process of the present disclosure is selected from gases that are inert to the probe molecule, the molecule for dead-time determination and the porous solid. Preferably, the carrier gas is selected from helium, nitrogen, argon or hydrogen. More preferably, the carrier gas is helium.

The probe molecule is injected into the carrier gas multiple times. This must be done at carrier gas flow rates sufficiently high so that the slope of the HETP equation (Equation (2)) is in the linear regime. These multiple injections should also be conducted with carrier gas flowrates sufficiently different in magnitude from each other to allow an accurate measurement of the variable "C" in equation (1). At least three injections of the probe molecules into the carrier gas are required. Preferably, the number of injections of probe molecule/carrier gas should be 3 to 20, more preferably 3 to 11. The magnitude of the difference between contiguous carrier flowrates is preferably at least 5 mL/min.

Vessel

The vessel in which the porous solid is placed for testing can generally be any container that facilitates contact of the probe molecule/carrier gas and the porous solid. Preferably, the shape of the vessel is cylindrical having a diameter of from 1 to 4 mm, preferably 1.5-3.0 mm. The length of the vessel is from 2-25 cm, preferably 3-15 cm. The mass of the porous solid is from 50 mg-2000 mg, preferably 70-280 mg. The materials of construction can be any that are compatible with the temperature and pressure of the testing, e.g., metal or glass.

Contacting the Porous Solid and the Probe Molecule

To measure the effective diffusion coefficient using the van Deemter model, the vaporized probe molecule is first injected into the carrier gas. The probe molecule can either be vaporized directly and then injected into the carrier gas or first dissolved in an inert solvent such as $CS_2$ or acetone, vaporizing the dissolved mixture and then injecting the vaporized material into the carrier gas. The vaporized probe molecule/carrier gas then flows through the vessel containing the porous solid, where the probe molecules diffuse into the pores of the porous solid and then out again. The probe molecule/carrier gas finally exits the vessel and flow past a detector which analyzes the stream to register the peak-width and retention time of the probe molecule. The same procedure is performed with the molecule for measuring the dead-time; only the retention time is determined. The detector is preferably a flame ionization detector or a thermal conductivity detector. More preferably, the flame ionization or thermal conductivity detector is part of a gas chromatography system. Contacting the probe molecule/carrier gas/molecule for measuring the dead-time/porous solid is preferably conducted at a temperature of 150 to 300° C., more preferably at 170-250° C.; and at a pressure of 0.5 to 2 bar, preferably 0.8 to 1.3 bar.

Evaluation of catalyst performance using measurement of the effective diffusion coefficient derived from the van Deemter model can be performed on all types of FCC catalysts. In the case of FCC equilibrium catalysts, the catalysts can be measured as received, i.e. with a carbon level up to 2.0 wt. % or calcined (carbon is burned off at temperatures >500° C.), i.e. carbon free. The diffusion measurements can also be performed on fresh FCC catalysts and FCC catalysts metallated in the laboratory with contaminant metals (V, Ni, Fe, Ca, and Na), and then deactivated in the laboratory. Such metal impregnation/deactivation protocols simulate FCC catalyst deactivation in commercial FCC units. The laboratory metallation and deactivation procedures can include those well known in the art, e.g., metallation by Mitchell impregnation, spray-impregnation, metal crack-on methods and deactivation methods such as Cyclic Propylene Steaming (ASTM D7206) and pure hydrothermal deactivations, as e.g., AM-1500 deactivation (ASTM D3907). In this way, catalyst evaluations can be conducted for an array of catalysts for a particular FCC unit such that the catalysts can be ranked according to their ability to provide bottoms upgrading, as evaluated by the techniques described in this disclosure.

Van Deemter Model Effective Diffusion Coefficient

In the process of the current disclosure, the concept of peak broadening proposed by van Deemter et al., "Longitudinal diffusion and resistance to mass transfer as causes of non-ideality in chromatography", Chemical Engineering Science, 5, 271-289, 1956 is used. The well-known equation derived for the height equivalent to a theoretical plate is given below as (Equation 1).

$$HETP = A + B/\mu + C*\mu \quad \text{(Equation 1)}$$

with

HETP, Height Equivalent to a Theoretical Plate [cm]

$\mu$, average linear velocity of the carrier gas [cm/s]

Figure 2:
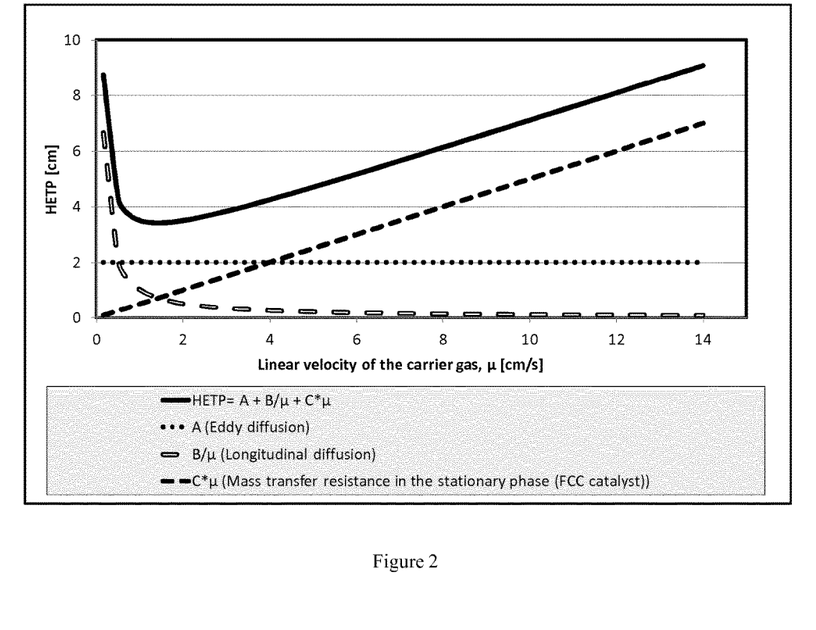
FIG. 2 illustrates HETP as a function of the linear gas velocity and the three individual terms of the van Deemter equation.

A, B and C are constants for a given system and are associated with eddy diffusion, longitudinal diffusion and mass transfer resistance in the stationary phase respectively, see FIG. 2.

As $B/\mu$ converges to zero at higher $\mu$, the equation simplifies to the linear Equation 2 in the range of high $\mu$, from which the parameter of interest, the effective diffusion coefficients of FCC catalysts, are derived.

$$HETP = A + C*\mu \quad \text{(Equation 2)}$$

HETP characterizes the separation efficiency of GC columns and is related to column length and the ratio of peak broadening to retention time. This parameter is calculated according to Equation 3.

$$HETP = Cat_{bl}[cm] * (b_{0.5}[s])^2 * (8*\ln 2)^{-1} * (t_{r\ prmol}[s])^{-2} \quad \text{(Equation 3)}$$

$Cat_{bl}$: Catalyst bed length [cm]

$b_{0.5}$: Half width of the peak [s]

$t_{r\ prmol}$: Retention time probe molecule [s]

The van Deemter model is a continuative consideration of the plate theory. It involves the dynamic response of HETP as a function of the average linear velocity of the carrier gas, as shown in FIG. 2, thereby facilitating distinguishing the three diffusion types: eddy diffusion, longitudinal diffusion and mass transfer resistance.

The average linear velocity $\mu$ is calculated according to Equation 4.

$$\mu = Cat_{bl}[cm] * (t_{r\ methane}[s])^{-1} \quad \text{(Equation 4)}$$

$Cat_{bl}$: Catalyst bed length [cm]

$t_{r\ methane}$: Retention time methane [s]

The diffusion process of interest in porous solids is characterized by the slope of the linear part of the van Deemter model as described above. HETP is therefore measured at several different and sufficiently large flow velocities $\mu$, allowing the estimation of the slope. HETP and $\mu$ are calculated for each flow rate and the slope C was estimated by linear regression, see Equation 2 and FIG. 2.

The van Deemter effective diffusion coefficients were derived according to Equation 5.

$$D_{eff} = 16 * APS^2[cm]^2 * k^2 * (\pi * C[s] * (1+k))^{-1} \quad \text{(Equation 5)}$$

APS=Average particle size [cm]

$k = (t_{r\ prmol}[s] - t_{r\ methane}(s)) / t_{r\ methane}[s]$ with $t_{r\ prmol}$ and $t_{r\ methane}$ from flow rate of 40 mL/min The following Examples further detail and explain the performance of the inventive process to evaluate catalytic performance. Those skilled in the art will recognize many variations that are within the spirit of the invention and scope of the claims.

Diffusion Measurements

Instrumentation

The chromatographic experiments were performed with an HP 6890 gas chromatograph equipped with a flame ionization detector, electronic pressure control for maintaining the correct flow rates, and automated sample injection. Helium was used as carrier gas. Quartzglas columns with the following dimensions were used: Length: 120 mm, external diameter: 8 mm, internal diameter: 3 mm.

FCC Catalyst Types

The FCC catalysts used contained rare-earth exchanged Y zeolites dispersed in an alumina sol matrix. The samples tested were equilibrium catalysts.

FCC Catalyst Pre-Treatment

Prior to the diffusion measurements, the equilibrium catalysts were heated in air for 3 h at 540° C. in a fixed bed. With this procedure catalyst inhibitors such as coke and nitrogen are removed from the sample.

Column Packing and Sample Conditioning

The columns were packed with 270 mg of FCC catalyst, fitted in the oven of the gas chromatograph and subsequently conditioned at 300° C. for 30 minutes under carrier gas flow. Thereafter, the samples were pre-equilibrated by 15 injections of the probe molecule.

Probe Molecule 1,2,4-Trimethylcyclohexane and phenanthrene dissolved in carbon disulfide (5 wt. % and 8 wt. % respectively) were used as individual probe molecules. The injection volume was 0.5 μL.

For each molecule the retention times and half widths of the peaks were determined at five different flow rates between 20 and 60 mL/min.

The measurements with 1,2,4-trimethylcyclohexane were performed at a 200° C. oven temperature, and those with phenanthrene at 350° C. The effective diffusion coefficient was measured at temperatures being much lower than those typically used in FCC operation (>500° C.) because under FCC temperatures the probe molecules would be converted to other products, rendering diffusion measurements impossible.

For the determination of the average linear velocity of the carrier gas, the retention times of methane were measured for each flow rate and temperature at which the probe molecule experiments were conducted. Methane is considered as a non-adsorbing molecule and having no diffusion limitations in FCC catalysts.

For Examples 3-5, the catalytic properties of the equilibrium catalysts were determined with an Advanced Cracking Evaluation™ (ACE) unit commercially available from Kayser Technology, Inc., 14207 Lake Scene Trail, Houston, Tex. 77059 USA. Testing was done at six different catalyst-to-oil ratios ranging from 3.5 to 7.5 g/g to generate conversion and yield response curves. The catalyst-to-oil ratios were varied by changing the mass of the catalyst while the total amount of feed and time-on-stream were kept constant at 1.5 g and 75 s, respectively. The catalyst bed temperature was adjusted to 540° C. The data reported in this study were obtained from interpolations at constant catalyst-to-oil ratio and at constant conversion. The feeds used for the different studies are compiled in Table 1.

TABLE 1

Feedstock properties

| | | Feed | | | |
| --- | --- | --- | --- | --- | --- |
| | | W | X | Y | Z |
| | | Example | | | |
| | | 1 | 2 | 3 | 4 |
| API gravity at 15° C. | | 22.7 | 24.6 | 21.2 | 25.0 |
| Density at 15° C. | kg/m$^3$ | 917.0 | 905.8 | 925.7 | 903.4 |
| Average molecular weight | g/Mol | 336 | 400 | 405 | 378 |
| $C_{aromatic}$(*) | % | 28.8 | 21.3 | 26.7 | 22.0 |
| Final boiling point | ° C. | 557 | 624 | 643 | 612 |
| UOPK factor | | 11.60 | 12.03 | 11.80 | 11.96 |

(*)calculated according to ASTM D 3238-95

Physical Characterization Methods

Surface area and pore volume distribution of the catalysts were determined by nitrogen sorption using a Micromeritics Tristar3000™ unit. The zeolite and matrix surface areas were calculated by the t-plot method (Harkins/Jura) using the pressure range $p/p_0$=0.06-0.35. The nitrogen pore volume was calculated from the volume of nitrogen adsorbed at the pressure point of $p/p_0$=0.97. The pore volume distribution was calculated from the desorption branch according to Barrett, Joyner and Halenda (BJH).

Particle size distribution and average particle size were determined by laser light scattering with a LS100Q apparatus from Coulter applying Fraunhofer theory.

The unit cell size of the zeolite Y was determined by X-ray diffraction (XRD) using a Bruker AXS D8 Advance analyzer according to the Standard ASTM D 3942-97 procedure.

The water pore volume was determined by adding water to a dry sample of a given weight. The water in between the particles was removed by centrifugation. The water pore volume represents the volume of water that displaces the air in the pores.

EXAMPLE 1

Impact of Molecule Size and Temperature on Diffusion

The effective diffusion coefficients of 1,2,4-trimethylcyclohexane and phenanthrene were determined for an equilibrium catalyst, the former at two temperatures. The results obtained are shown in Table 2.

TABLE 2

Impact of molecule size and temperature on diffusion
Catalyst B

| Effective Diffusion Coefficients ($D_{eff}$) | | |
| --- | --- | --- |
| $D_{eff}$: 1,2,4-Trimethylcyclohexane; 200° C. | mm$^2$/min | 10 |
| $D_{eff}$: 1,2,4-Trimethylcyclohexane; 350° C. | mm$^2$/min | 42 |
| $D_{eff}$: Phenanthrene; 350° C. | mm$^2$/min | 6 |
| Physical and Chemical Properties | | |
| Zeolite Surface area | m$^2$/g | 107 |
| Matrix Surface area | m$^2$/g | 26 |
| Unit Cell Size | Å | 24.29 |
| Pore Volume H$_2$O | mL/g | 0.35 |
| Average particle size | μm | 78 |
| Al$_2$O$_3$ | wt. % | 49.9 |
| RE$_2$O$_3$ | wt. % | 3.3 |
| Na | wt. % | 0.34 |
| V | mg/kg | 5258 |
| Ni | mg/kg | 3316 |
| Fe | wt. % | 0.68 |

The magnitude of the effective diffusion coefficients categorizes them to be in the Knudsen regime, which is characterized by the fact that the pore diameter is smaller than the mean free path of the probe molecule used, and collisions between the probe molecules and pore walls occur more frequently than among the molecules themselves. The Knudsen regime can be expected in mesopores and macropores of FCC catalysts under typical FCC conditions. Thus, the intraparticle diffusion in FCC catalysts does not depend on the diffusion in micropores. Such an intracrystalline surface diffusion and solid diffusion in the zeolite part of the FCC catalyst would result in lower effective diffusion coefficients.

With respect to the impact of temperature and molecule size, diffusion was accelerated by temperature increase and lowered by increase of the molecule size.

EXAMPLE 2

Figure 3:
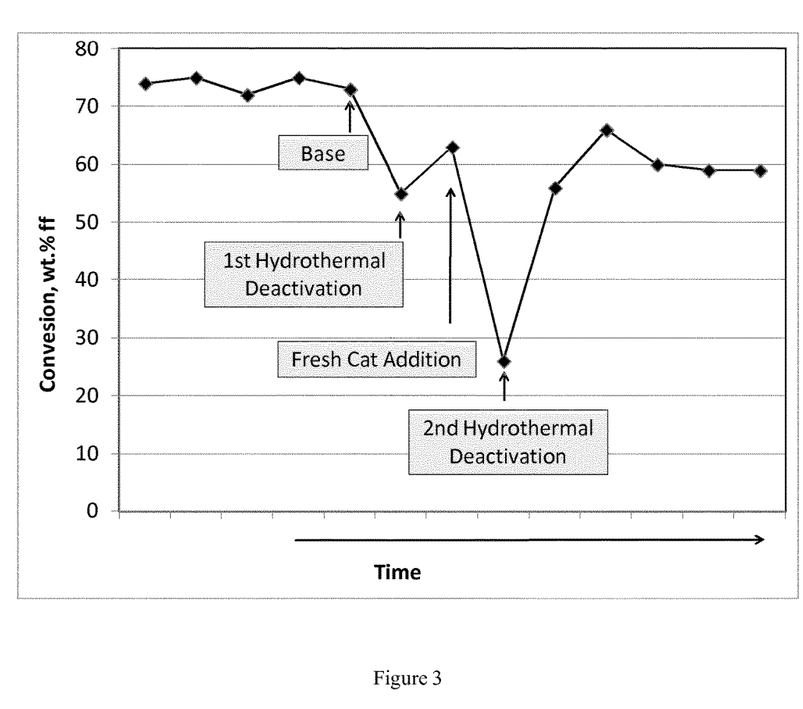
FIG. 3 illustrates the effect of hydrothermal deactivation on conversion in Refinery W, Example 2.

The inventory of a commercial FCC unit experienced a severe hydrothermal deactivation. Thereafter, the deactivated catalyst was partially replaced by fresh catalyst to recover catalyst activity. Then a second severe hydrothermal deactivation occurred. The effect of the hydrothermal deactivation incidents on conversion are shown in FIG. 3. The unit equilibrium catalysts for these were analyzed to evaluate conventional parameters, which conventionally reflect the changes in catalyst quality induced by this deactivation-recovery cycle, such as surface area, pore volume and effective diffusion coefficient. The data obtained are given in Table 3.

TABLE 3

Effects of hydrothermal deactivation in Refinery W, Example 2.

| | | Catalyst | | | |
|---|---|---|---|---|---|
| | | C | D | E | F |
| Event | | Base | 1st hydrothermal deactivation | Fresh cat addition | 2nd hydrothermal deactivation |
| Effective Diffusion Coefficients ($D_{eff}$) | | | | | |
| $D_{eff\,(1,2,4\text{-}Trimethylcyclohexane)}$ | mm$^2$/min | 47 | 15 | 24 | 3 |
| MAT testing on Feed W | | | | | |
| Conversion | wt. % ff | 73 | 55 | 63 | 27 |
| Physical and Chemical Properties | | | | | |
| Total Surface Area | m$^2$/g | 174 | 59 | 96 | 21 |
| Pore Volume N$_2$ | mL/g | 0.16 | 0.12 | 0.11 | 0.08 |
| Pore Volume H$_2$O | mL/g | 0.39 | 0.36 | 0.36 | 0.32 |
| Average particle size | μm | 97 | 92 | 92 | 90 |
| Al$_2$O$_3$ | wt. % | 40.8 | 40.9 | 40.7 | 41.1 |
| RE$_2$O$_3$ | wt. % | 1.5 | 1.6 | 1.7 | 1.7 |
| Na | wt. % | 0.21 | 0.19 | 0.22 | 0.19 |
| V | mg/kg | 500 | 583 | 528 | 501 |
| Ni | mg/kg | 189 | 243 | 226 | 240 |
| Sb | mg/kg | 36 | 28 | 34 | 33 |
| Fe | wt. % | 0.49 | 0.51 | 0.52 | 0.54 |

The effective diffusion coefficient, conversion, surface area and pore volume were reduced after each deactivation event. Following fresh cat additions, the effective diffusion coefficient, conversion and surface area increased. Hence, the effective diffusion coefficients clearly reflect the conventional conversion and surface area data. Since contaminant metals were very low, the changes in effective diffusion coefficient, conversion and surface area data can be attributed to the hydrothermal deactivation itself.

EXAMPLE 3

Refinery X switched from catalyst type G to H. Catalytic and physical properties as well as the effective diffusion coefficients of corresponding equilibrium catalysts taken from the FCC unit inventory are given in Table 4.

TABLE 4

Effects of catalyst change in Refinery X, Example 3

| | | Catalyst | |
|---|---|---|---|
| | | G | H |
| Effective Diffusion Coefficients ($D_{eff}$) | | | |
| $D_{eff\,(1,2,4\text{-}Trimethylcyclohexane)}$ | mm$^2$/min | 29 | 60 |
| ACE testing on Refinery X Feed | | | |
| Conversion[a] | wt. % ff | 69 | 76 |
| C$_1$-C$_4$[b] | wt. % ff | 18.3 | 16.1 |
| Gasoline[b] | wt. % ff | 44.9 | 48.2 |
| LCO[b] | wt. % ff | 11.8 | 14.5 |
| C$_4$-Olefinicity[b] | % | 52 | 59 |

TABLE 4-continued

Effects of catalyst change in Refinery X, Example 3

| | | Catalyst | |
|---|---|---|---|
| | | G | H |
| Physical and Chemical Properties | | | |
| Zeolite Surface area | m$^2$/g | 90 | 78 |
| Matrix Surface area | m$^2$/g | 29 | 37 |
| Unit Cell Size | Å | 24.32 | 24.34 |
| Pore Volume H$_2$O | mL/g | 0.31 | 0.31 |
| Average particle size | μm | 82 | 59 |
| Al$_2$O$_3$ | wt. % | 47.7 | 47.0 |
| RE$_2$O$_3$ | wt. % | 2.8 | 2.9 |
| Na | wt. % | 0.38 | 0.27 |

TABLE 4-continued

Effects of catalyst change in Refinery X, Example 3

|  |  | Catalyst | |
|---|---|---|---|
|  |  | G | H |
| V | mg/kg | 3920 | 3320 |
| Ni | mg/kg | 3829 | 3551 |
| Sb | mg/kg | 1334 | 27 |
| Fe | wt. % | 0.66 | 0.47 | interpolated at catalyst-to-oil ratio = 6
[b]interpolated at 70 wt. % ff conversion The catalytic data show catalyst H to have higher activity and to produce more gasoline, LCO (light cycle oil), and higher product olefinicity. Normally such differences are attributable to changes in unit cell size and zeolite surface area, where the former is the main driving force for catalyst activity, and also steers catalyst selectivity. Briefly, increasing unit cell size enhances activity and hydrogen transfer rates. As a consequence of the latter, gasoline olefins are reduced, leading to a lower crackability of this fraction. Thus, higher gasoline yields are expected with increasing unit cell size. The literature also reports LCO yields to be enhanced by low unit cell size catalysts.

The difference in activity between catalyst G and H can be related to the difference in unit cell size, however, the ranking in olefinicity cannot be rationalized with this parameter. The olefinicities are enhanced with increasing unit cell size, i.e., the ranking is reversed to that expected from the changes in unit cell sizes. Another phenomenon is that the sample which produced more olefins, i.e. gasoline of higher crackability, had the highest gasoline yield.

The conflicting unit cell size vs. selectivity findings is explained by the effective diffusion coefficients. The effective diffusion coefficients given in Table 4 suggest faster diffusion of the gasoline and LCO molecules through catalyst H, and thus less secondary cracking and hydrogen transfer in these two fractions. Hence, higher product olefinicity, more gasoline as well as LCO and less $C_1$-$C_4$ were obtained in case of the high unit cell size catalyst.

Figure 4:
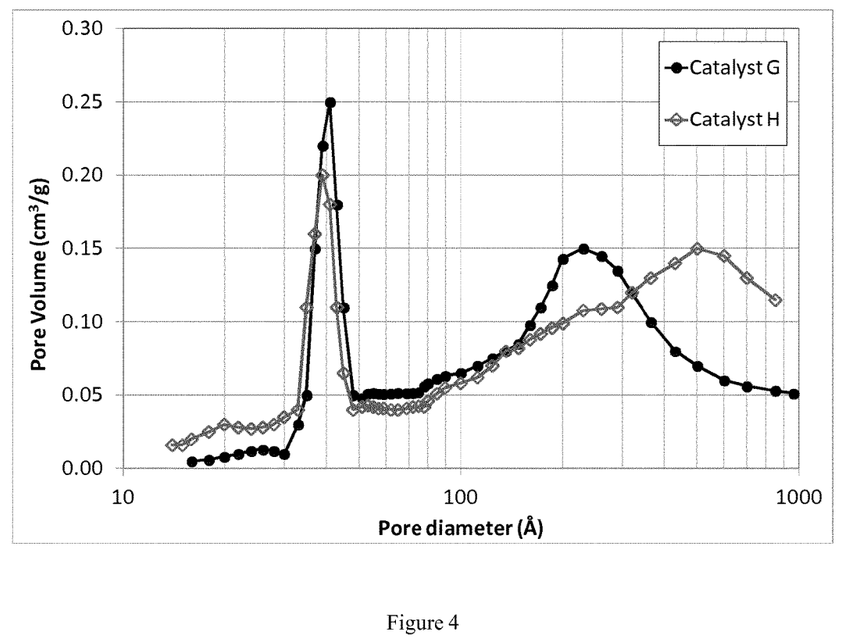
FIG. 4 illustrates BJH pore volume distribution (nitrogen sorption), Example 3.

The pore volume distributions given in FIG. 4 show no pronounced difference in mesoporosity to which the shifts in selectivities and effective diffusion coefficients could be attributed. Hence, this data suggests that effective diffusion coefficients and selectivities are determined by other parameters than mesoporosity determined by nitrogen sorption, such as e.g., macroporosity, which cannot be measured by nitrogen sorption methods.

EXAMPLE 4

Figure 5:
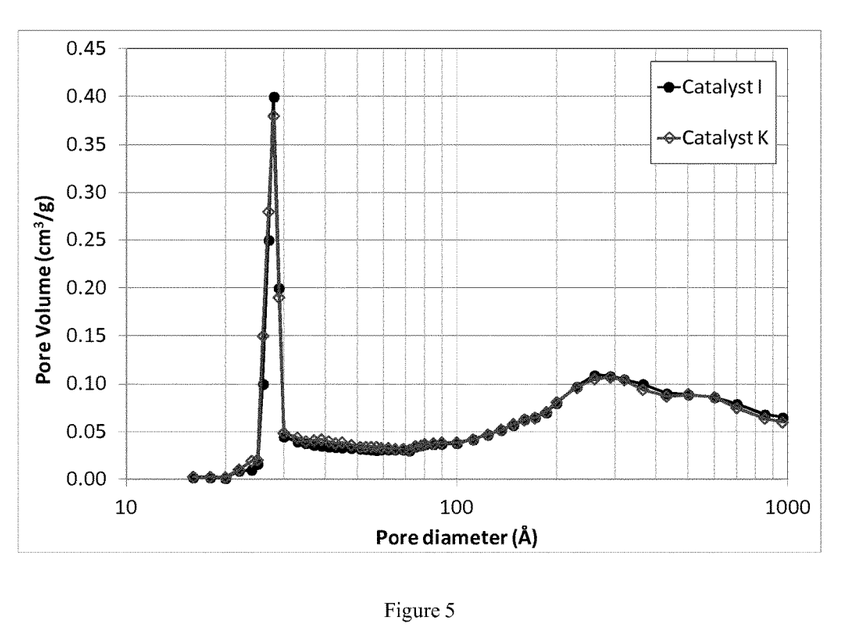
FIG. 5 illustrates a BJH pore volume distribution (nitrogen sorption), Example 4.

Refinery Y switched from catalyst type I to K. Catalytic and physical properties as well as the effective diffusion coefficients of corresponding equilibrium catalysts taken from the FCC unit inventory are given in Table 5 and FIG. 5.

TABLE 5

Effects of catalyst change in Refinery Y, Example 4.

|  |  | Catalyst | |
|---|---|---|---|
|  |  | I | K |
| Effective Diffusion Coefficients ($D_{eff}$) | | | |
| $D_{eff(1,2,4-Trimethylcyclohexane)}$ | mm²/min | 23 | 73 |
| ACE testing on Refinery Y Feed | | | |
| Conversion[a] | wt. % ff | 67 | 69 |
| $C_1$-$C_4$[b] | wt. % ff | 19.1 | 18.4 |
| Gasoline[b] | wt. % ff | 45.0 | 46.1 |
| LCO[b] | wt. % ff | 16.4 | 16.7 |
| $C_4$-Olefinicity[b] | % | 51 | 54 |
| Physical and Chemical Properties | | | |
| Zeolite Surface area | m²/g | 99 | 99 |
| Matrix Surface area | m²/g | 24 | 24 |
| Unit Cell Size | Å | 24.33 | 24.33 |
| Pore Volume H₂O | mL/g | 0.34 | 0.34 |
| Average particle size | μm | 82 | 85 |
| Al₂O₃ | wt. % | 46.4 | 49.6 |
| RE₂O₃ | wt. % | 2.9 | 3.7 |
| Na | wt. % | 0.25 | 0.24 |
| V | mg/kg | 5180 | 5184 |
| Ni | mg/kg | 2840 | 2973 |
| Sb | mg/kg | 666 | 519 |
| Fe | wt. % | 0.44 | 0.36 |

[a]interpolated at catalyst-to-oil ratio = 6
[b]interpolated at 70 wt. % ff conversion This example illustrates catalyst changeover, where the physical and textural properties (unit cell size, zeolite and matrix surface area, mesoporosity) of both catalyst types are virtually identical. The catalytic data however, show differences in activity, $C_1$-$C_4$, gasoline, LCO and hydrogen transfer which again, as in Example 3, cannot be explained by changes in unit cell size, zeolite surface area and mesoporosity. Instead, they are explained by the differences in effective diffusion coefficient.

Catalyst K has a higher effective diffusion coefficient than catalyst I and the arguments given in Example 3 for the selectivity differences hold in this comparison as well. The catalyst with the higher effective diffusion coefficient had less secondary cracking reactions and hydrogen transfer due to shorter residence times of the molecules in the FCC particle. Thus, this sample produced higher product olefinicity, more gasoline as well as LCO and less $C_1$-$C_4$.

EXAMPLE 5

Figure 6:
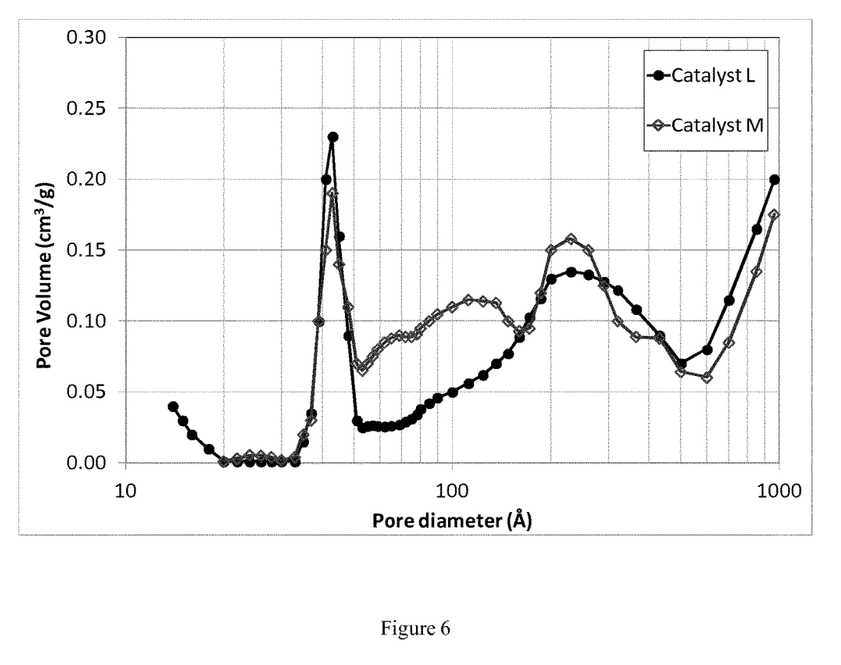
FIG. 6 illustrates a BJH pore volume distribution (nitrogen sorption), Example 5.

Refinery Z switched from catalyst L to M. Catalytic and physical properties as well as the effective diffusion coefficients of corresponding equilibrium catalysts taken from the FCC unit inventory are given in Table 6 and FIG. 6.

TABLE 6

Effects of catalyst change in Refinery Z, Example 5.

|  |  | Sample | |
|---|---|---|---|
|  |  | L | M |
| Effective Diffusion Coefficients ($D_{eff}$) | | | |
| $D_{eff(1,2,4-Trimethylcyclohexane)}$ | mm²/min | 32 | 67 |
| ACE testing on Refinery Z Feed | | | |
| Conversion[a] | wt. % ff | 75 | 76 |
| $C_1$-$C_4$[b] | wt. % ff | 21.1 | 20.7 |

TABLE 6-continued

Effects of catalyst change in Refinery Z, Example 5.

|  |  | Sample | |
|---|---|---|---|
|  |  | L | M |
| Gasoline[b] | wt. % ff | 49.0 | 49.3 |
| LCO[b] | wt. % ff | 14.3 | 14.6 |
| $C_4$-Olefinicity[b] | % | 51 | 52 |
| Physical and Chemical Properties | | | |
| Zeolite Surface area | $m^2/g$ | 100 | 77 |
| Matrix Surface area | $m^2/g$ | 28 | 40 |
| Unit Cell Size | Å | 24.32 | 24.37 |
| Pore Volume $H_2O$ | mL/g | 0.36 | 0.35 |
| Average particle size | µm | 89 | 85 |
| $Al_2O_3$ | wt. % | 46.8 | 52.7 |
| $RE_2O_3$ | wt. % | 2.8 | 3.3 |
| Na | wt. % | 0.50 | 0.38 |
| V | mg/kg | 951 | 1227 |
| Ni | mg/kg | 1857 | 1483 |
| Sb | mg/kg | 14 | 11 |
| Fe | wt. % | 0.56 | 0.47 | interpolated at catalyst-to-oil ratio = 6
[b]interpolated at 75 wt. % ff conversion From the differences in unit cell sizes between catalysts L and M, it would be expected for catalyst M to produce much lower product olefinicity, higher gasoline yield and lower LCO. However, with the exception of gasoline, these selectivities show tendencies in the opposite direction. Again, the only explanation can be obtained from the effective diffusion coefficients. The sample with the high unit cell size (catalyst M) has the higher effective diffusion coefficient.

Hence, less secondary cracking reactions and hydrogen transfer and thus higher product olefinicity, more gasoline as well as LCO and less $C_1$-$C_4$ were obtained.

In summary, Examples 2-5 show that effective diffusion coefficients can explain selectivity shifts in cases where the traditional approach involving unit cell size, zeolite surface area and mesoporosity appear to have reached their limit. The results suggest that diffusion limitations in the mesopore and macropore system of FCC catalysts have a pronounced impact on catalyst performance. The impact of the zeolite part of the FCC catalyst on catalyst performance is attributed to reactions of the feed and intermediate products on its external surface area and thus being part of the meso- and macropore system in FCC catalysts.

Other features, advantages and embodiments of the invention disclosed herein will be readily apparent to those exercising ordinary skill after reading the foregoing disclosure. In this regard, while specific embodiments of the invention have been described in considerable detail, variations and modifications of these embodiments can be effected without departing from the spirit and scope of the invention as described and claimed.

Embodiments of the Invention

1. A process for evaluating the catalytic performance of a porous solid, the process comprising:
    (a) injecting a vaporized probe molecule and a molecule for dead-time determination into a carrier gas having a first flowrate, thereby forming a combined gas;
    (b) feeding the combined gas to a vessel containing the porous solid, wherein the combined gas contacts the porous solid, thereby forming a contacted gas;
    (c) analyzing the contacted gas after it exits the vessel in a detector to measure the peak-width and the retention time of the probe molecule, and the retention time of the molecule for dead-time determination;
    (d) repeating steps (a)-(c) wherein for each set of repeated steps the carrier gas has a flowrate different than the first flowrate and other succeeding flowrates; and
    (e) calculating an effective diffusion coefficient for the porous solid,
        wherein the porous solid is reactively inert toward the probe molecule and the molecule for dead-time determination.
2. The process of (1) wherein the probe molecule has a boiling point of 150° C. to 250° C.
3. The process of (1) or (2) where the molecule for dead-time determination is selected from methane, ethane or propane.
4. The process of (1), (2) or (3) where the catalyst bed geometry is cylindrical having a diameter from 1 to 4 mm and a length from 2 to 25 cm.
5. The process of (3) where the molecule for dead-time determination is methane.
6. The process of any one of (2)-(5) wherein the probe molecule is selected from 1,2,4-Trimethylcyclohexane, t-decaline, Adamantan or phenanthrene.
7. The process of (6), wherein the probe molecule is 1,2,4-Trimethylcyclohexane.
8. The process of any one of (1)-(7), wherein the porous solid comprises a fluid cracking catalyst.
9. The process of (8), wherein the fluid cracking catalyst is an equilibrium catalyst.
10. The process of (8) or (9) wherein the fluid cracking catalyst has a matrix surface area of 10 to 150 $m^2/g$ and a zeolite surface area of 20 to 450 $m^2/g$.
11. The process of any one of (1)-(10) wherein the first carrier gas flow rate is from 5 to 50 mL/min.
12. The process of any one of (1)-(11) wherein the carrier gas is selected from helium, nitrogen, argon and hydrogen.
13. The process of any one of (1)-(12) where steps (a)-(c) are repeated 5 to 20 times.
14. The process of any one of (1)-(13) wherein the probe molecule has a size of 5 to 15 Å.
15. A process for adjusting fresh catalyst additions to an FCC unit, the process comprising:
    (a) injecting a vaporized probe molecule and a molecule for dead-time determination into a carrier gas having a first flowrate, thereby forming a combined gas;
    (b) feeding the combined gas to a vessel containing deactivated FCC catalyst, wherein the combined gas contacts the deactivated FCC catalyst, thereby forming a contacted gas, the probe molecule and the molecule for dead-time determination being reactively inert to the deactivated FCC catalyst;
    (c) analyzing the contacted gas after it exits the vessel in a detector to measure the peak-width and the retention time of the probe molecule, and the retention time of the molecule for dead-time determination;
    (d) repeating steps (a)-(c) wherein for each set of repeated steps the carrier gas has a flow rate different than the first flowrate and other succeeding flowrates;
    (e) calculating an effective diffusion coefficient for the FCC catalyst; and
    (f) changing the fresh catalyst additions to the FCC unit based on the difference between a target effective diffusion coefficient and the calculated effective diffusion coefficient.
16. The process of (15) which is as further defined in any one of (2)-(10) or (11)-(14) above.

We claim:

1. A process for evaluating the catalytic performance of a porous solid catalyst, the process comprising:
   (a) injecting a vaporized probe molecule and a molecule for dead-time determination into a carrier gas having a first flowrate, thereby forming a combined gas;
   (b) feeding the combined gas to a vessel containing the porous solid catalyst, wherein the combined gas contacts the porous solid catalyst, thereby forming a contacted gas;
   (c) analyzing the contacted gas after it exits the vessel in a detector to measure the peak-width and the retention time of the probe molecule, and the retention time of the molecule for dead-time determination;
   (d) repeating steps (a)-(c) wherein for each set of repeated steps the carrier gas has a flowrate different than the first flowrate and other succeeding flowrates; and
   (e) calculating an effective diffusion coefficient for the porous solid catalyst, wherein the porous solid catalyst is reactively inert toward the probe molecule and the molecule for dead-time determination and wherein the probe molecule has a size of 5 to 15 Å.

2. The process of claim 1 wherein the probe molecule has a boiling point of 150° C. to 250° C.

3. The process of claim 2 wherein the probe molecule is selected from 1,2,4-Trimethylcyclohexane, t-decalin, Adamantane or phenanthrene.

4. The process of claim 3, wherein the probe molecule is 1,2,4-Trimethylcyclohexane.

5. The process of claim 1 where the molecule for dead-time determination is selected from methane, ethane or propane.

6. The process of claim 5 where the molecule for dead-time determination is methane.

7. The process of claim 1 where the catalyst bed geometry is cylindrical having a diameter from 1 to 4 mm and a length from 2 to 25 cm.

8. The process of claim 1, wherein the porous solid catalyst comprises a fluid cracking catalyst.

9. The process of claim 8, wherein the fluid cracking catalyst is an equilibrium catalyst.

10. The process of claim 8 wherein the fluid cracking catalyst has a matrix surface area of 10 to 150 m²/g and a zeolite surface area of 20 to 450 m²/g.

11. The process of claim 1 wherein the first carrier gas flow rate is from 5 to 50 mL/min.

12. The process of claim 1 wherein the carrier gas is selected from helium, nitrogen, argon and hydrogen.

13. The process of claim 1 where steps (a)-(c) are repeated 5 to 20 times.

14. The process of claim 1 wherein the probe molecule has a size of 8 to 10 Å.

15. A process for adjusting fresh catalyst additions to an FCC unit, the process comprising:
   (a) injecting a vaporized probe molecule and a molecule for dead-time determination into a carrier gas having a first flowrate, thereby forming a combined gas;
   (b) feeding the combined gas to a vessel containing deactivated FCC catalyst, wherein the combined gas contacts the deactivated FCC catalyst, thereby forming a contacted gas, the probe molecule and the molecule for dead-time determination being reactively inert to the deactivated FCC catalyst;
   (c) analyzing the contacted gas after it exits the vessel in a detector to measure the peak-width and the retention time of the probe molecule, and the retention time of the molecule for dead-time determination;
   (d) repeating steps (a)-(c) wherein for each set of repeated steps the carrier gas has a flow rate different than the first flowrate and other succeeding flowrates;
   (e) calculating an effective diffusion coefficient for the FCC catalyst; and
   (f) changing the fresh catalyst additions to the FCC unit based on the difference between a target effective diffusion coefficient and the calculated effective diffusion coefficient.

16. The process of claim 15 wherein the probe molecule has a boiling point of 150 to 250° C.

17. The process of claim 16 wherein the probe molecule is selected from 1,2,4-Trimethylcyclohexane, t-decalin, Adamantane or phenanthrene.

18. The process of claim 17, wherein the probe molecule is 1,2,4-Trimethylcyclohexane.

19. The process of claim 15 where the molecule for dead-time determination is selected from methane, ethane or propane.

20. The process of claim 19 where the molecule for dead-time determination is methane.

21. The process of claim 15, wherein the FCC catalyst is a fluid cracking catalyst.

22. The process of claim 21, wherein the fluid cracking catalyst is an equilibrium catalyst.

23. The process of claim 21 wherein the fluid cracking catalyst has a matrix surface area of 10 to 150 m²/g and a zeolite surface area of 20 to 450 m²/g.

* * * * *